United States Patent [19]
Usui et al.

[11] Patent Number: 4,593,012
[45] Date of Patent: Jun. 3, 1986

[54] PRODUCTION OF HYDROCARBON-SOLUBLE SALTS OF MOLYBDENUM FOR EPOXIDATION OF OLEFINS

[75] Inventors: Masahiro Usui; Yasuhiko Higashio, both of Chiba, Japan

[73] Assignee: Atlantic Richfield Company, Los Angeles, Calif.

[21] Appl. No.: 708,480

[22] Filed: Mar. 5, 1985

[30] Foreign Application Priority Data

Mar. 9, 1984 [JP] Japan .................................. 59-46145

[51] Int. Cl.$^4$ ............................................. B01J 31/04
[52] U.S. Cl. .................................. 502/167; 502/170; 549/529
[58] Field of Search ................................ 502/167, 170

[56] References Cited

U.S. PATENT DOCUMENTS 3,453,218  7/1969  Sheng et al. .................... 502/170 X
3,595,891  7/1971  Cavitt .............................. 502/170 X
3,956,180  5/1976  Cavitt .................................. 502/171

FOREIGN PATENT DOCUMENTS 422437  3/1974  U.S.S.R. .

Primary Examiner—Patrick P. Garvin
Attorney, Agent, or Firm—Michael S. Jarosz

[57] ABSTRACT

Production of novel hydrocarbon-soluble salts, especially adapted for use as catalysts in the epoxidation of olefinic compounds with an organic hydroperoxide, by reaction of an ammonium molybdate with a carboxylic acid in the presence of an organic amine at specified elevated temperatures while removing water.

12 Claims, No Drawings

PRODUCTION OF HYDROCARBON-SOLUBLE SALTS OF MOLYBDENUM FOR EPOXIDATION OF OLEFINS

BACKGROUND OF THE INVENTION

The production of oxirane compounds such as propylene oxide and its higher homologs is described in Kollar U.S. Pat. No. 3,351,635. In accordance with the Kollar process, the oxirane compound may be prepared by epoxidation of an olefinically unsaturated compound (for example, propylene) by use of organic hydroperoxide and a suitable metal catalyst, such as a molybdenum compound. Kollar teaches that activity of the metal catalyst disclosed therein for expoxidation of primary olefins is high and can lead to high selectivity of propylene to propylene oxide. These selectivities are obtained at high conversions of hydroperoxide (50% or higher) which conversion levels are important for commercial utilization of this technology. In accordance with the Kollar process, the epoxidation reaction proceeds under pressure in a liquid state, and accordingly, a liquid solution of the metal catalyst is desired.

In the preparation of these compounds, for example, molybdenum salts, for the aforementioned purpose, various techniques have been used, many of which have been found to be extremely difficult to carry out efficiently on a commercial scale, and hence expensive, particularly for preparing hydrocarbon soluble compositions containing a high molybdenum content. In addition, a number of the above-identified catalyst materials, for example, molybdenum acid salts prepared by reaction of a molybdenum compound with a carboxylic acid as disclosed in Becker U.S. Patent Re 30,642, suffer from various disadvantages including poor solubility in the reaction medium and low metal concentration.

In an effort to increase the concentration of molybdenum in the reaction medium in the catalytic epoxidation of olefins, preparations of epoxidation catalysts from comparatively expensive molybdenum metal have been reported in the prior art, for example, in Sheng et al U.S. Pat. Nos. 3,453,218 and 3,434,975. However, the use of low cost starting materials, such as ammonium molybdate, in the preparation of epoxidation catalyst solutions soluble in hydrocarbons has been hampered due to the slow rate of dissolution, precipitation of solids as a result of decomposition of the dissolved molybdenum species, and unsatisfactory low molybdenum concentration in these solutions. Accordingly, a number of preparations of organic-soluble molybdenum containing catalysts from a variety of oxygen containing molybdenum compounds have been reported in the prior art. In this connection, attention is directed to Bonetti U.S. Pat. No. 3,480,563 which discloses the preparation of such catalysts by reacting molybdenum trioxide with a monohydric primary saturated acyclic alcohol having from 4 to 22 carbon atoms in the molecule or with a mono- or polyalkylene glycol monoalkyl ether or mixtures thereof. An earlier patent to Price et al, U.S. Pat. No. 3,285,942 discloses the preparation of glycol molybdates of specified formula by reaction of an alpha- and beta-alkane diol of from 2 to 18 carbon atoms with molybdic acid or related molybdenum compounds in the presence of an organic nitrogen base. Maurin et al U.S. Pat. No. 3,822,321 describes the oxidation of olefins with a hydroperoxide using a molybdenum catalyst prepared by reaction of molybdenum containing compound, such as molybdic acid or salt, with a polyalcohol. Epoxidation of olefins by use of a molybdenum catalyst, prepared by reacting an oxygen-containing molybdenum compound with amine (or an amine N-oxide) and alkylene glycol is also described by Lines et al in U.S. Pat. No. 4,157,346. Hagstrom et al U.S. Pat. No. 3,991,090 and 4,009,122 disclose a method of preparing molybdenum compound by reaction of an oxygen containing molybdenum compound with a polyhydroxy compound having vicinal hydroxyl groups in the presence of a hydrohalic acid. French Pat. No. 1,550,166 discloses that molybdic acid esters, and especially glycol esters of molybdic acid, provide certain advantages over previously known catalysts to effect epoxidation employing organic hydroperoxides in reaction with olefinic compounds. Cavitt U.S. Pat. No. 4,046,783 discloses the use in olefin epoxidation reactions of an oxidized alkyl molybdate complex catalyst prepared by contacting an inorganic molybdenum compound with an aliphatic monohydric alcohol in the presence of a weak base to form a lower oligometric alkyl molybdate compound which is then oxidized to form an oxidized alkyl molybdate complex catalyst. Also, ammonium molybdate epoxidation catalyst solutions are described in U.S. Pat. Nos. 3,956,180 and 2,795,552.

When an ammonium molybdate is heated together with a hydrocarbon carboxylic acid, the ammonium molybdate reacts with the carboxylic acid to produce a molybdenum solution. However, this reaction requires a considerable length of time in order to produce a homogeneous molybdenum solution and, when the ratio of the ammonium molybdate to hydrocarbon carboxylic acid exceeds a certain level, the molybdenum precipitates within the reaction system after a prolonged period and as a result, a homogeneous solution containing a high concentration of molybdenum cannot be obtained.

Accordingly, it is an object of the present invention to provide for the production of novel molybdenum-containing salt catalyst compositions which are characterized by improved dissolution rates in organic hydrocarbon solutions, high molybenum concentrations in organic solutions, and provide stable dissolved molybdenum species free of precipitation of solids due to decomposition, thereby resulting in improved and increased catalyst preparation and productivity.

An additional object of the present invention is to provide a process for the epoxidation of olefinic compounds by use of the hydrocarbon-soluble molybdenum salt catalyst compositions of the invention, thereby resulting in increased yield and selectivity to desired alkylene oxide, e.g. propylene oxide, in the epoxidation of a primary olefin, e.g. propylene, while at the same time reducing production of undesired by-products.

SUMMARY OF THE INVENTION

It has now been discovered that stable solutions of molybdenum-containing salts, especially adapted for use as homogeneous epoxidation catalyst compositions, and which contain increased quantities of molybdenum in such catalyst composition than heretofore obtainable, may be readily prepared by reacting a commercially available ammonium molybdate reactant with a specified hydrocarbon carboxylic acid in the presence of an organic amine. Accordingly, it has been discovered, in accordance with the present invention, that a relatively inexpensive source of molybdenum, namely an ammonium molybdate, may be directly reacted with the aforedescribed class of organic carboxylic acid in the presence of specified concentrations of an organic amine at certain elevated temperatures to produce molybdenum salt compositions which are readily dissolved at improved dissolution rates in a hydrocarbon medium and are particularly stable in organic solutions and capable of providing high molybdenum content in resulting catalyst compositions, thereby rendering the same especially adapted for use as catalysts in the epoxidation of olefinic compounds with an organic hydroperoxide oxidizing agent.

DETAILED DESCRIPTION OF THE INVENTION

As used in the present specification and the annexed claims, the term "stable catalyst solution" is intended to mean a molybdenum-containing salt solution which will not precipitate an appreciable amount, i.e. less than about 0.1% of the molybdenum contained in the solution, of molybdenum, upon standing at ambient temperature for 1 to 30 days.

The process of the present invention directed to the preparation of the hydrocarbon soluble molybdenum salts comprises the direct reaction of an ammonium molybdate reactant with carboxylic acid in the presence of an organic amine at elevated temperatures. It is a critical feature of the present process that free water be removed during the reaction; this includes any water that may be initially present, as well as water that might be formed during the reaction.

The carboxylic acids contemplated by this invention are carboxylic acids containing 4 to about 30 carbon atoms including hydrocarbon aliphatic, alicyclic and aromatic carboxylic acids. The aliphatic acids may be lower aliphatic acids such as butyric, isobutyric, valeric, caproic and the like; intermediate aliphatic acids of from 7 to 11 carbon atoms, such as oleic, suberic, octanoic, sebacic, palmitic, abiethic, linolenic, enanthic, dodecanoic, hexadecanoic, decosanoic, tetracosanoic, tricosanoic and the like. The alicyclic acids generally may contain from 4 to 12 carbon atoms such as cyclohexanoic, cyclodecanoic, cyclododecanoic and the like. The aromatic acids may generally contain one or two fused rings and contain from 7 to 14 carbon atoms wherein the carboxyl group may or may not be attached to the ring; such as benzoic, 1- or 2-napthoic, o, m-, and p-toluic, phenylacetic, 1- or 2-naphthalene acetic, phenylbutyric acid, and the like. Monocarboxylic acids such as the lower aliphatic, and intermediate aliphatic and alicyclic acids are preferred.

The ammonium molybdate reactant of the above process may be present as commercially available ammonium molybdate (($NH_4$)$_2$$Mo_2$$O_4$), ammonium dimolybdate (($NH_4$)$_2$$Mo_2$$O_7$) or paramolybdate (($NH_4$)$_6$$Mo_7$$O_{24}$·4$H_2$O).

The organic amine employed in preparing the molybdenum-containing salt of the invention may generally be represented by the formula:

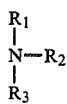 (Formula I)

wherein each of $R_1$, $R_2$ and $R_3$ is independently selected from hydrogen, unsubstituted and substituted alkyl of 1 to 10, preferably 1 to 6 carbon atoms and unsubstituted and substituted aryl of 6 to 12, preferably 6 to 8, carbon atoms; with the proviso that at least one of $R_1$, $R_2$ and $R_3$ is not hydrogen.

The preferred amines of Formula I above are those wherein each of $R_1$, $R_2$ and $R_3$ is hydrogen or alkyl, particularly unsubstituted alkyl such as methyl, ethyl, propyl, butyl, pentyl, hexyl and the like. Especially preferred are the tertiary alkyl amines wherein each alkyl group contains 1 to 4 carbon atoms. Illustrative of these are aliphatic amines such as n-hexylamine, triethylamine, diethylamine, dibutylamine, tributylamine and hexamethylenediamine; and aromatic amines such as aniline, diphenylamine, triphenylamine, benzylamine and dibenzylamine. Also employable in the method of the present invention are cyclic amines such as pyridine, α-picoline and piperidine. The organic amine is employed in a molar ratio of about 0.05 to about 1.0, preferably about 0.1 to about 0.5 with respect to the hydrocarbon carboxylic acid.

As indicated previously, removal of water is a critical feature of the process for preparation of the molybdenum-containing salt compositions of the invention. If the reaction is carried out without the removal of water, extremely long reaction times may be required in preparation of these compositions and, more importantly, the stability of the resultant composition may not be achieved. However, although water removal appears necessary, the manner in which water is removed is unimportant. Therefore, one may employ any known technique for water removal during this preparatory reaction. A particularly desirable manner in which water may be removed from the reaction mixture and which significantly reduces the reaction time for formation of the desired molybdenum salt involves employment, in conventional manner, of a gas purge comprising a molecular oxygen-containing gas, such as air, or an inert gas, such as nitrogen. Particularly preferred is use of a molecular oxygen-containing gas, purge, for example, air, which not only removes water in the reaction mixture, but also maintains dissolved molybdenum in its higher oxidation state, thus allowing for higher loading of molybdenum in the resultant molybdenum salt solution. In the absence of sufficient oxygen, or air, reduction of the molybdenum salt occurs, forming dark blue colloidal solutions which are capable of being oxidized by air, or a molecular oxygen-containing gas, at the temperatures of the reaction. In general, any amount of oxygen sufficient to reoxidize the reduced low valent molybdenum of the reduced molybdenum compound to hexavalent molybdenum may be employed. Alternatively, water may be removed by the use of dehydrating agents, such as calcium chloride, or by use of an azeotropic agent. Any azeotropic agent which is inert to the reaction itself may be employed in the process. Suitable azeotropic compounds include benzene or arylalkyl compounds, such as lower alkyl benzenes containing of from 1 to 3 alkyl groups and each alkyl group containing of from 1 to 4 carbon atoms, such as ethylbenzene, xylene, cumene, or any other straight or branched chain hydrocarbon, such as an alkane of from 5 to 12 carbon atoms, e.g. hexane, octane and decane. The quantity of azeotropic agent necessary depends upon the amount of water to be removed and will vary from one system to another, which quantity can be readily determined by one skilled in the art. In general, it may not be necessary to remove all water which is present in or may be formed during the reaction. The amount of water removed will depend upon the weight concentration of molybdenum desired in the molybdenum salt produced and the duration of the reaction. The more concentrated molybdenum-containing salt solutions to be produced in the reaction will require removal of greater quantities of water, with removal of substantially all water present or formed during the reaction being optimum for obtaining the most concentrated molybdenum containing salt compositions; hence, such procedure will provide reaction mixtures containing up to about 1%, generally up to about 0.5%, and preferably, up to about 0.1%, by weight of water, based on the weight of the reaction mixture.

The ammonium molybdate reactant, carboxylic acid and organic amine, in general, may be reacted in the presence of an inert solvent, typically present as one or more of the above-identified azeotropic agents. However, no such solvent is required when the carboxylic acid and amine employed are liquids at the temperature of the reaction.

The reaction between the ammonium molybdate reactant and carboxylic acid in the presence of the organic amine should be controlled at a temperature of from about 150° C. to about 250° C. In its preferred aspects, the reaction is carried out at a temperature of from about 170° C. to about 220° C., and especially between about 185° C. and 210° C. Any minimum temperature which provides the desired reaction may be employed, but temperatures higher than about 250° C. are not recommended due to the susceptibility of dissolved molybdenum salt to thermally decompose at such temperatures, forming solutions which are not completely homogeneous, and hence, incapable of forming stable catalyst solutions. It is particularly convenient to use atmospheric pressures although pressures above or below atmospheric may also be employed; if desired. With increase in temperature, shorter reaction times may be employed, although, in general, reaction times in the range of from about 2 to 36 hours, or longer, preferably 10 to 24 hours, are sufficient to produce the desired organic soluble molybdenum salt composition.

The quantity of ammonium molybdate reactant employed for reaction with the carboxylic acid may range from about 1:4 to about 1:12 or more, and preferably from between about 1:6 and 1:8 on a molar basis. In general, the hydrocarbon soluble molybdenum salt compositions of the invention obtained by the aforedescribed process may contain of from about 5 to about 15 percent molybdenum, based on the weight of the composition.

The molybdenum-containing compositions prepared in accordance with the process of the present invention have been found to be suitable as catalysts for epoxidation of olefins, illustratively propylene, to produce the corresponding oxirane compound, e.g., propylene oxide, for example, at high yields and conversions, without production of high quantities of undesirable by-products. In general, the compositions of the present invention when employed in conventional manner as is known in the art, are suitable as catalysts in the epoxidation of olefinic compounds having the general formula:

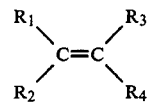

where $R_1$, $R_2$, $R_3$ and $R_4$ may be hydrogen, alkyl, aryl arylalkyl, alkaryl, alkenyl, alkadienyl or similar radicals having functional groups, in accordance with the process described and claimed in Kollar U.S. Pat. No. 3,351,635, the disclosure of which is hereby incorporated by reference. Illustrative acylic olefinic hydrocarbons which may be epoxidized are the aliphatic normally gaseous olefins such as propylene, the butylenes and the higher liquid and solid olefins.

In addition to being employed as fresh catalyst solution in the above-described epoxidation reaction, the molybdenum-containing catalyst composition of the present invention finds particular use as make-up catalyst to be employed together with molybdenum-containing catalyst concentrate or residue. Such concentrations or residues are obtained from previous epoxidation processes employing a molybdenum epoxidation catalyst wherein the epoxidation reaction mixture is resolved into product fractions, including a heavy liquid fraction containing the catalyst, subjecting the heavy liquid fraction containing the catalyst to evaporation, such as a wiped film evaporation, at elevated temperatures until at least about 60% by weight of said fraction is evaporated overhead, and recycling the evaporation residue to said epoxidation, as described and claimed in Levine et al U.S. Pat. No. 3,819,663, the disclosure of which is hereby incorporated by reference. When employed as make-up catalyst, the catalyst composition of the present invention is employed in quantities up to about 90, and preferably up to about 50 percent, by weight, of the catalyst composition being recycled to the epoxidation reaction.

In order to illustrate practice of the invention, the following examples are provided. It is to be understood that the examples are merely illustrative and are not intended to be restrictive of the invention herein disclosed and as defined by the claims following hereto. Parts and percentages are by weight, and temperatures are in degree Centigrade, unless otherwise specified.

EXAMPLE 1

A mixture of 5.5 parts of ammonium molybdate, 18.5 parts of naphthenic acid (Wako Chemical Co., Ltd.), and 4.0 parts of tri-n-butylamine was heated at 200° for 10 hours with constant stirring of the contents while removing water formed during the reaction, thereby resulting in a hydrocarbon-soluble molybdenum salt.

When 20 ml of ethylbenzene were added to the above-prepared salt, a homogeneous solution containing 6 weight % of molybdenum was obtained. This solution did not form a precipitate even when allowed to stand in air for one month.

COMPARATIVE EXAMPLE 1

A mixture of 5.5 parts of ammonium molybdate and 22.5 parts of naphthenic acid (Wako Chemical Co., Ltd.) was heated to 200° for 10 hours with constant stirring of the contents while removing water formed during the reaction. When 20 ml of ethylbenzene were added to the above-prepared salt, a considerable amount of precipitate was formed. The molybdenum concentration of the solution after filtration of the precipitate was 35 weight % and, when this solution was allowed to stand in air for one month, a considerable amount of sludge was formed.

EXAMPLES 2-9

Molybdenum salts of the invention were prepared by employing 4.0 parts of the respective organic amines listed in Table I below, instead of the tri-n-butylamine used in Example 1. The reaction conditions employed for preparing the salts were identical to those of Example 1, except that the organic amines were used in place of the tri-n-butylamine.

TABLE I

| Example | Organic Amine | Solution Product Characterization following dilution with 20 ml of Ethylbenzene |
|---|---|---|
| 2 | di-n-butylamine | homogeneous |
| 3 | n-hexylamine | homogeneous |
| 4 | hexamethylenediamine | slight formation of precipitate |
| 5 | aniline | homogeneous |
| 6 | diphenylamine | homogeneous |
| 7 | triphenylamine | homogeneous |
| 8 | benzylamine | homogeneous |
| 9 | dibenzylamine | homogeneous |

EXAMPLE 10

An epoxidation reaction was conducted in conventional manner by using the hydrocarbon-soluble salt of molybdenum prepared in Example 1. In the procedure, 20 parts of the hydrocarbon-soluble molybdenum salt of Example 1 were added to 50 parts of ethylbenzene solution containing 35 weight % of ethylbenzene hydroperoxide ("EBHP") and the epoxidation reaction was effected at 120° for one hour after introducing 46 parts of propylene. The following results were obtained; EBHP convertibility of 99.6% and propylene oxide selectivity of 86.5% (based on EBHP).

COMPARATIVE EXAMPLE 2

The epoxidation reaction of Example 10 was carried out by using 20 parts of molybdenum naphthenate (Nippon Climax Molybdenum Co., Ltd.) instead of the hydrocarbon-soluble molybdenum salt of Example 1. The reaction conditions employed were identical to those of Example 10. The following results were obtained: EBHP convertibility of 95.9% and propylene oxide selectivity of 86.8% (based on EBHP).

COMPARATIVE EXAMPLE 3

To 50 parts of ethylbenzene solution containing 35 weight % of ethylbenzene hydroperoxide were added 20 parts of the molybdenum salt prepared in Comparative Example 1, and epoxidation was effected by heating the reaction contained after introducing 46 parts propylene to the mixture at 102° for one hour. The following results were obtained: EBHP convertibility of 98.7% and propylene oxide selectivity of 80.1% (based on EBHP).

COMPARATIVE EXAMPLE 4

An epoxidation reaction was conducted by adding 5 parts of tri-n-butylamine to the reaction mixture of Comparative Example 3. The other reaction conditions were identical to those of Comparative Example 3, except for the addition of the tri-n-butylamine. The following results were obtained: EBHP convertibility of 98.2% and propylene oxide selectivity of 76.4% (based on EBHP).

Examples 1-9 inclusive, (as compared with Comparative Example 1) show the production of stable, hydrocarbon-soluble molybdenum salts in accordance with the process of the invention, and Example 10, (together with Comparative Examples 2 and 3) shows that a typical molybdenum salt catalyst produced in accordance with this invention provides ethylbenzene conversions to EBHP and propylene oxide selectivity at least as good or better than standard organic soluble molybdenum catalysts. Comparative Example 4 demonstrated that as compared with the results of Example 10, the addition of the organic amine directly to the epoxidation reaction greatly decreases the propylene oxide selectivity.

What is claimed is:

1. The method of producing a hydrocarbon-soluble molybdenum-containing salt, useful as a catalyst for the epoxidation of an olefinic compound with an organic hydroperoxide, which comprises reacting an ammonium molybdate with a carboxylic acid in the presence of an organic amine at a temperature from about 150° C. to about 250° C., while removing water.

2. The process of claim 1 wherein, said carboxylic acid is a hydrocarbon monocarboxylic acid containing of from 4 to about 30 carbon atoms and said molybdate is ammonium molybdate.

3. The process of claim 2 wherein said organic amine corresponds to the formula: $R_1R_2R_3N$ wherein each of $R_1$ $R_2$ and $R_3$ is independently selected from the group consisting of hydrogen, alkyl of 1 to 10 carbon atoms, and aryl of 6 to 12 carbon atoms, with the proviso that at least one of $R_1$, $R_2$, and $R_3$ is not hydrogen.

4. The process of claim 3 wherein water is removed by employment of a purge gas selected from the group consisting of a molecular oxygen containing gas and an inert gas through the reaction mixture.

5. The process of claim 3 wherein water is removed by employment of an azeotropic agent.

6. The process of claim 3 wherein water is removed by use of a dehydrating agent.

7. The process of claim 5 wherein said azeotropic agent is a member selected from the group consisting of an alkyl substituted benzene and an alkane.

8. The process of claim 7 wherein said reaction is effected at a temperature of between about 170° C. and 220° C.

9. The process of claim 8 wherein said carboxylic acid is an alkanoic acid containing of from 4 to about 12 carbon atoms.

10. The reaction product comprising the hydrocarbon-soluble molybdenum containing salt produced by the process of claim 1.

11. The reaction product comprising the hydrocarbon-soluble molybdenum containing salt produced by the process of claim 3.

12. The reaction product comprising the hydrocarbon-soluble molybdenum-containing salt produced by the process of claim 9.

* * * * *